Nov. 24, 1936. J. F. HISCOX Plant Pat. 208
ROSE
Filed June 19, 1936
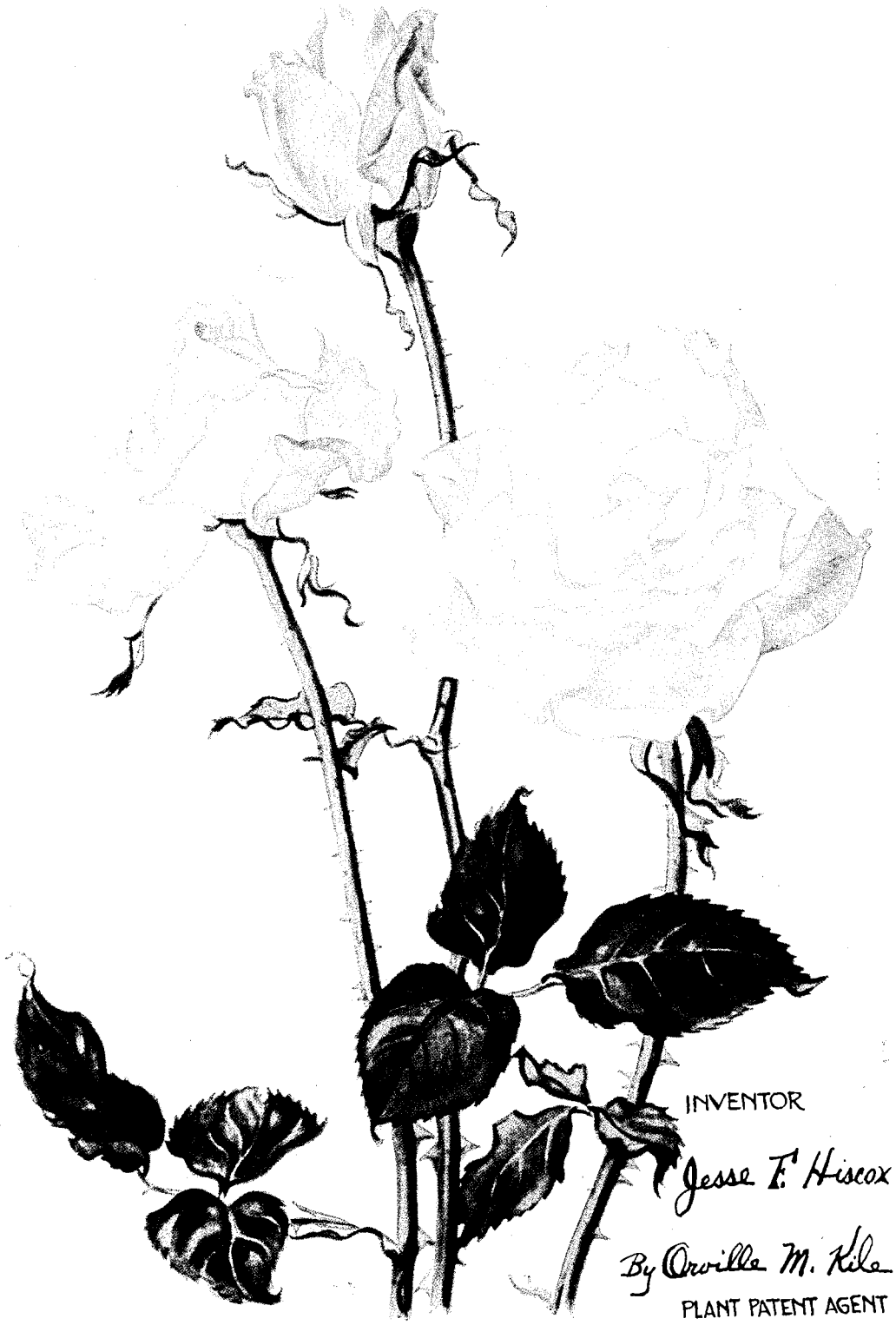

Patented Nov. 24, 1936

Plant Pat. 208

UNITED STATES PATENT OFFICE

208

ROSE

Jesse F. Hiscox, East Patchogue, N. Y.

Application June 19, 1936, Serial No. 86,166

1 Claim. (Cl. 47—61)

The present invention relates to a new and improved variety of hybrid tea rose plant, involving interesting and novel color effects and other desirable qualities. It is a sport of Joanna Hill and has some of the qualities of its parent plant, although it differs in several definite points. The novel qualities claimed have been observed through several generations and have been shown to be fixed.

The accompanying illustration shows two buds and an open flower, together with stem and foliage, depicted in as nearly true form and color as is possible. The three views of the flower show the different colorings in the different stages of development.

The following is a detailed description of this new variety and all color references are to Ridgway's Color Standards and Nomenclature.

*The plant*

*Form.*—Bush, upright, tall.

*Habits of growth.*—Similar to Joanna Hill but a more vigorous grower.

*Blooming habit.*—Continuous.

*Foliage:*—

*Leaves.*—Under surface is Pois Green (Plate XLI); upper surface Dark Cress Green (Plate XXXI) with reddish edge. Compound, with 3 to 5 leaflets; small—terminal leaflet measures 1¾ to 2 inches in length.

*Leaflets.*—Oval; closely serrate; inclined to crinkle.

*Rachis.*—Medium in length; usually with two or three sharp spines on under side.

*Stipules.*—Medium, with sharp points.

*Stems.*—Long and stiff; Calla Green (Plate V).

*Thorns.*—Many large red thorns, irregularly placed and downward pointing. Pompeian Red (Plate XIII). Many small thorns, spines and prickles on peduncle.

*Sepals.*—Moderately recurved; moderately foliaceous; Dark Cress Green (Plate XXXI).

*The flower*

Bud:—

*Size.*—About 2 inches long.

*Shape.*—Tight bud is long and slender.

*Peduncle.*—Long, 4 to 6 inches; strong, heavy; thickly covered with small pinkish thorns and spines irregularly placed.

*Color.*—Upon opening, the color of the bud approaches Rose Red (Plate XII), although a little more brilliant than this shade. Each of the two outer petals has a "lip" which turns back abruptly. This lip is velvety and of a darker hue, approaching Carmine (Plate I) or Pomegranite Purple (Plate XII). As the bud opens the color lightens and the inner petals of a different color begin to show, giving the flower a different color effect. The half-opened flower shows the two outer petals, which formed the outside of the bud, of Rose Red (Plate XII) streaked with Apricot Orange (Plate XIV). These streaks are formed by exposure to the light during the tight bud stage. The part of these two petals which is first visible remains dark while the portion covered in the earlier stage is lighter and sometimes of a different color. Occasionally a small portion of one or two other of the outer petals is exposed in the bud form and streaks are formed on these petals also as the flower opens. As the buds open further they show the outer petals as having streaks of Rose Color (Plate XII) and Deep Rose Pink (Plate XII). All the petals have a spot of Lemon Chrome at the base, more clearly visible on the inner side of the petal.

Bloom:—

*Size.*—Opens to 4½ to 5½ inches across.

*Form.*—Pointed or high centered at first, later opening into flat cupped form.

*Petalage.*—Twenty to twenty-five petals in April in the inventor's greenhouse.

*Petals:*—

*Substance.*—Thick.

*Arrangement.*—Moderately loose; no petaloids in center.

*Shape.*—Round.

*Persistence.*—Drop cleanly in a few days.

*Color.*—The fully opened flower gives an entirely different color effect from that of the bud and opening flower. The small inner petals are Flesh Pink to Coral Pink (Plate XIII) on the outer side and on the inside they are Pinkish Buff (Plate XXIX) with a golden suffusion radiating from the spot of Lemon Chrome (Plate IV) at the base of each petal.

*Fragrance.*—Strong but pleasing.

*Reproductive organs*

*Stamens.*—Many; arranged irregularly about many pistils.

*Filaments.*—Long; yellow with reddish base.

*Anthers.*—Large; yellow; placed vertical on filaments.

*Pollen.*—Scarce or lacking.

*Pistil.*—Compound.

*Styles.*—Many; bunched; uneven length; reddish tips.

*Stigma.*—Many.

*Hips.*—Large; tapering; Parrot Green (Plate VI).

Having thus disclosed my invention, what I claim as new is:

The variety of rose plant as described, characterized particularly by its distinctive color of bud and bloom; its strong and pleasant fragrance; its vigorous growth; and its long, strong stems.

JESSE F. HISCOX.